United States Patent [19]

Shigetoh et al.

[11] Patent Number: 5,571,727

[45] Date of Patent: Nov. 5, 1996

[54] LABELLING COLORS FOR DETECTING COCAINE OR METHAMPHETAMINE, METHOD OF PREPARING THE SAME AND DETECTOR FOR COCAINE OR METHAMPHETAMINE

[75] Inventors: Nobuyuki Shigetoh, Hirakata; Hiroshi Nakayama, Toyonaka; Jinsei Miyazaki, Higashiosaka; Tadayasu Mitsumata, Hirakata, all of Japan

[73] Assignee: Matsushita Electric Industrial Co., Ltd., Osaka, Japan

[21] Appl. No.: 319,976

[22] Filed: Oct. 7, 1994

[30] Foreign Application Priority Data

Oct. 7, 1993  [JP]  Japan .................................. 5-251513
Dec. 16, 1993  [JP]  Japan .................................. 5-316194
Jul. 25, 1994  [JP]  Japan .................................. 6-172437

[51] Int. Cl.⁶ ..................... G01N 33/542; G01N 33/533; C07D 401/06; C07D 209/14
[52] U.S. Cl. .......................... 436/537; 436/546; 436/816; 546/126; 548/490; 548/491
[58] Field of Search ............. 546/126; 548/491, 548/490; 436/537, 546, 816

[56] References Cited

U.S. PATENT DOCUMENTS 3,833,863  9/1974  Webster et al. .
3,904,613  9/1975  Schmitt .................................. 548/491
4,344,879  10/1982  Mohr et al. ........................... 548/491

FOREIGN PATENT DOCUMENTS 61-201166  9/1986  Japan .
30-50558-A  3/1991  Japan .
60-59486  3/1994  Japan .
61-10156  4/1994  Japan .
2074340  10/1981  United Kingdom .

OTHER PUBLICATIONS

U. Mushkalko et al., Ukr. Khim. Zh. (Russ. Ed), vol. 52, No. 5, pp. 509–513 (1986).
J. March, Advanced Organic Chemistry, Reactions, Mechanisms, and Structure, pp. 326 and 327, McGraw-Hill, Inc., NY (1977).
R. Morrison et al., Organic Chemistry, Second Edition, pp. 732 and 733, Allyn and Bacon, Inc., Boston (1967).

*Primary Examiner*—Mary E. Ceperley
*Attorney, Agent, or Firm*—Fish & Richardson P.C.

[57] ABSTRACT

A labelling color for detecting cocaine of Formula (I)

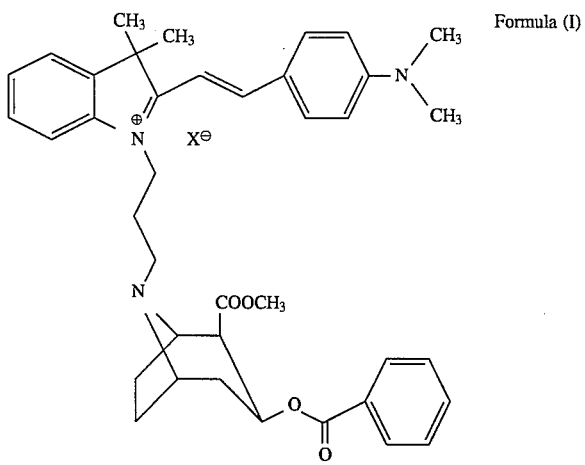

wherein X represents a halogen, and a method of detecting methamphetamine, including the steps of adding a labelling color of Formula (II)

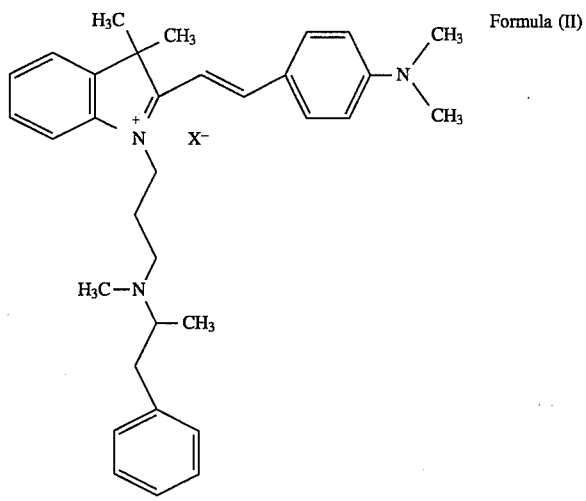

wherein X represents an anion to a first solution of methamphetamine antibody to form a labelling color-methamphetamine antibody complex, measuring the fluorescence of the first solution, adding a sample containing an unknown amount of methamphetamine to the first solution to form a second solution, measuring the fluorescence of the second solution, and correlating any change in the fluorescence between the first and second solutions to the concentration of methamphetamine in the sample.

16 Claims, 5 Drawing Sheets

LABELLING COLORS FOR DETECTING COCAINE OR METHAMPHETAMINE, METHOD OF PREPARING THE SAME AND DETECTOR FOR COCAINE OR METHAMPHETAMINE

FIELD OF THE INVENTION

This invention relates to labelling colors for detecting cocaine or methamphetamine, a method of using the labelling colors, and a detector for cocaine or methamphetamine using the labelling colors. The colors are applicable to immunoassay or other biochemical experiments.

BACKGROUND OF THE INVENTION

In the field of labelling colors to detect methamphetamine (MA), Japanese Unexamined Patent Publication No. HEI 3-223673 proposes an MA substituted with a dansyl group. This dansylized MA (DNS-MA) emits a 525 nm fluorescence intensity in a 330 nm excited state. The DNS-MA bonding to an MA-antibody changes its fluorescence intensity. When the DNS-MA encounters a newly added MA molecule, the DNS-MA leaves the antibody, reducing the intensity of 525 nm fluorescence. Observation of this change enables detection of even a very small amount of MA.

However, the detection capacity of such a method using DNS-MA is decreased by the presence of foreign substances. There are so many naturally-occurring substances having a fluorescence around 525 nm that it was difficult to detect MA from such a test sample contaminated with such substances. Further, such a method has not been able to detect cocaine because an appropriate labelling color for detecting cocaine by immunoassay was not developed.

SUMMARY OF THE INVENTION

To solve the above-noted problems, the invention provides labelling colors for detecting cocaine or MA, intermediates of the labelling colors, methods of preparing the labelling colors, method of using the colors, and a detector for cocaine or MA using the colors.

The first labelling color of the invention is the compound of Formula I wherein X represents a halogen atom. This compound is used to detect cocaine.

The second labelling color of the invention is the compound of Formula wherein X represents an anion. This compound is used to detect MA.

The method of using the labelling color of Formula I or II comprises the steps of adding the labelling color of Formula I or II to a first solution of cocaine antibody or MA antibody to form a labelling color-antibody complex, measuring the fluorescence of the first solution, adding a sample containing an unknown amount of cocaine or MA to the first solution to form a second solution, measuring the fluorescence of the second solution, and correlating any change in the fluorescence between the first and second solutions to the concentration of cocaine or MA in the sample. Both colors of Formulas I and II can be used in combination so that cocaine and MA are detected at a time.

The detector for cocaine and/or MA of the invention comprises containers for storing each of a first solution containing the labelling color of Formula I and/or the labelling color of Formula II and a second solution containing cocaine antibody and/or MA antibody, an eluting means for eluting a sample with a buffer to form a sample solution, a reactor for reacting said sample solution with said first solution containing a labelling color and said solution containing at least one antibody, a supplying means for supplying each of the sample solution and said solution containing at least one antibody to said reactor, and a fluorescent detector for measuring fluorescences of the first and second solutions, and a mixture of the sample solution and the first and second solutions.

It is preferable in the detector that said supplying means is a syringe pump and a valve.

It is preferable in the detector that said reactor is a rectangular cell having an outlet and a hole in an upper face and a nozzle for exhaustion at the bottom.

It is preferable in the detector that a stirring means for stirring the sample solution and the first and second solutions is provided in the reactor, and said stirring means is driven by magnetic force.

It is preferable in the detector that a thermostat using a Peltier device is provided in the reactor.

It is preferable in the detector that the containers and supplying means are provided within an air-conditioning thermostat.

The intermediate of the compound of Formula I is a propyl halide derivative of Formula III Formula III wherein $X_1$ and $X_2$ represents the same or different halogen atom.

The first intermediate of the compound of Formula II is a methanesulfonate derivative of Formula IV Formula IV wherein X is an anion.

The second intermediate of the compound of Formula II is a hydroxy derivative of Formula V Formula V wherein X represents an anion.

The third intermediate of the compound of Formula II is an acetyl derivative of Formula VI Formula VI wherein X represents an anion.

The method of preparing a labelling color of Formula I comprises the steps of dissolving a propyl halide derivative of Formula III in an organic solvent, adding norcocaine of Formula VII Formula VII to the solution, and heating the solution.

The method of preparing a propyl halide derivative of Formula III, comprising the steps of dissolving a trimethylindolenium salt of Formula VIII Formula VIII wherein $X_1$ and $X_2$ is the same or different halogen atom, and dimethylamino benzaldehyde of Formula IX Formula IX in an organic solvent, and heating the solution.

The method of preparing a labelling color of Formula II comprises the steps of providing a methanefulfonate derivative of Formula IV and substituting methamphetamine for a methanesulfonate group of the compound of Formula IV in an acidic solvent.

DETAILED DESCRIPTION OF THE INVENTION

The labelling colors of Formula I and H (hereinafter CCIMC and MAIMC, respectively) have fluorescence in the long-wave region of about 590 nm. CCIMC of Formula I has chemical affinity for cocaine antibody: however, that affinity is less strong than the affinity CCIMC has for cocaine. Therefore, when no cocaine is in a solution, CCIMC bonds to cocaine antibody, thus increasing the fluorescence intensity of the solution. Once cocaine is added, CCIMC leaves the cocaine antibody, and in turn bonds to cocaine because of the stronger affinity between cocaine and CCIMC. The solution can reduce the fluorescence intensity to the initial level of intensity. The change in fluorescence intensity depends upon the amount of cocaine added. Consequently, cocaine is detected by monitoring the change in fluorescence intensity of the solution. MA is detected using MAIMC of Formula H in the same manner.

In particular, MAIMC of Formula H absorbs light having a wavelength around 550 nm and has fluorescence in the longwave region around 590 nm. Consequently, the color compound is less susceptible to impurities having absorbance in the ultraviolet region, and to light diffusion due to impurities, which is conspicuous in that region.

The compound of Formula III having a halogen substituent provides an intermediate suitable for preparing the labelling compound of Formula I.

The compound of Formula IV having a methanesulfonate substituent provides an intermediate suitable for preparing the labelling compound of Formula II.

The compound of Formula V having a hydroxyl group has reactivity for acid chlorides. The compound of Formula V readily reacts with methanesulfonic anhydride to form the compound of Formula IV. The compound of Formula V is effectively prepared using the compound of Formula VI having an acetyl group. It appears that the compound of Formula V is directly prepared by the reaction between N-hydroxypropyl-2,2,3-trimethylindolenin and dimethylbenzaldehyde of Formula IX. However, this reaction actually does not proceed because the hydroxyl group of N-hydroxypropyl-2,2,3-trimethylindolenin inhibits the reaction. Therefore, the hydroxyl group of N-hydroxypropyl-2,2,3-trimethylindolenin is first substituted with an acetyl group, and then, the substituted indolenin derivative reacts with dimethylbenzaldehyde to form the compound of Formula VI. The compound of Formula VI is hydrolyzed to form the compound of Formula V. In other words, the compound of Formula VI provides a high yield of the skeleton of the color, i.e., the compound of Formula V.

The compound of Formula VII is prepared by mixing, for example, chloroiodopropane and about 0.5 to 2 mole parts trimethyl indolenine and heating the mixture at about 60° to 100° C. for about 1 to 5 hours.

The compound of Formula m is prepared by mixing the compound of Formula VIII in an organic solvent such as ethanol solution and equimole parts of the compound of Formula IX, that is, dimethylamino benzaldehyde and heating the mixture at about 60° to 100° C. In this reaction, the dimethylamino group of dimethylamino benzaldehyde works as a base instead of a conventional base, i.e., pyridine. Therefore, the compound of Formula III is readily provided without pyridine.

The labelling compound of Formula I is prepared by mixing, for example, the iodopropyl derivative of Formula III wherein $X_2$ is an iodine atom in an organic solvent such as chloroform and about 2 to 10 mole parts norcocaine of Formula VII and heating the mixture at about 60° to 100° C. for about 5 to 12 hours.

The compound of Formula VI is prepared by mixing the compound of Formula VIII wherein $X_2$ is substituted with an acetyl group in a basic organic solvent such as pyridine and equimole parts of the compound of Formula IX and heating the mixture at about 110° to 150° C.

The compound of Formula V is prepared by mixing the compound of Formula VI in an organic solvent such as ethanol and an appropriate amount of an alkali solution such as an aqueous solution of sodium hydroxide, stirring the mixture at room temperature under normal pressure for about 1 to 2 hours, adjusting the pH of the reaction mixture, and lastly removing the solvent.

The compound of Formula IV is prepared by mixing the compound of Formula V in an organic solvent such as chloroform and about 2 to 20 mole parts methanesulfonic anhydride and stirring the mixture at room temperature or a low temperature around 4° C. under normal pressure for 1 to 10 days.

The labelling compound of Formula II is prepared by mixing the compound of Formula IV in an acidic solvent such as acetic acid and about 2 to 20 mole parts methamphetamine and heating the mixture at about 50° to 80° C. for about 2 to 20 hours.

The detector of the invention using the labelling colors readily detects cocaine, MA and their derivatives with high sensitivity.

Now, the detector of the invention will be explained. A syringe pump and a valve are suitable for the supplying means of the detector to supply quickly solutions from the containers to the reactors. A rectangular cell having an outlet and a hole in an upper face and a nozzle for exhaustion at the bottom is suitable for the reactor of the detector. Control of opening and shutting the supplying means and the nozzle enables sequential examination of different solutions. A stirring means for stirring solutions in the reactor, preferably a magnetic stirrer, shortens the time of handling. A thermostat using a Peltier device in the reactor is helpful for detection at a constant temperature. Further, the containers and supplying means of the detector are preferably provided within an air-conditioning thermostat so that the whole process of detection is carried out in a certain environment.

Figure 1:
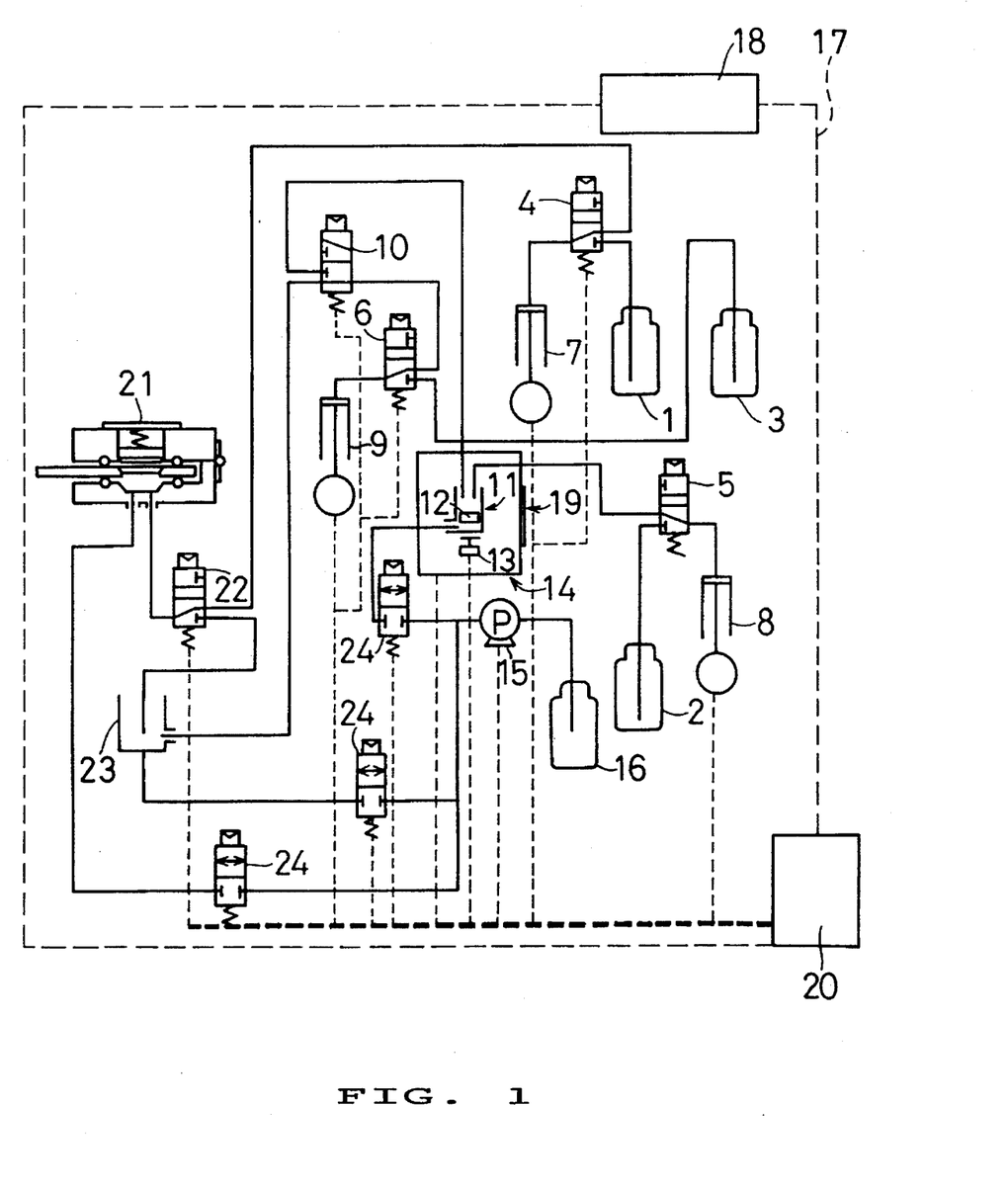
FIG. 1 is a schematic block diagram showing a detector for cocaine or MA of one preferred embodiment.

Referring to FIG. 1, the whole detector is disposed in air-conditioned room 17, which is kept at 25° C. by air-conditioner 18. Containers 1 and 3 contain a color solution, and container 2 contains an antibody solution. A color solution in container 1 is for use in eluting a sample. Container 1 is connected with valve 4 and pump 7. Container 2 is connected with valve 5 and pump 8. Container 3 is connected with valve 6 and pump 9. Container 1 is also associated with elution device 21 through valves 4 and 22. Reservoir 23 is placed under elution device 21. Reservoir 23 is associated with reactor 11 inside of fluorescent detector 14 through switching valve 10. Magnetic stirrer bar 12 and magnetic stirrer 13 as stirring means are placed inside and outside of reactor 11. Peltier device 19 keeps reactor 11 at 25° C. Each of reactor 11, elution device 21 and reservoir 23 is associated with discharge tank 16 through valve 24 and discharge pump 15. Reference numeral 25 denotes cables.

Figure 2:
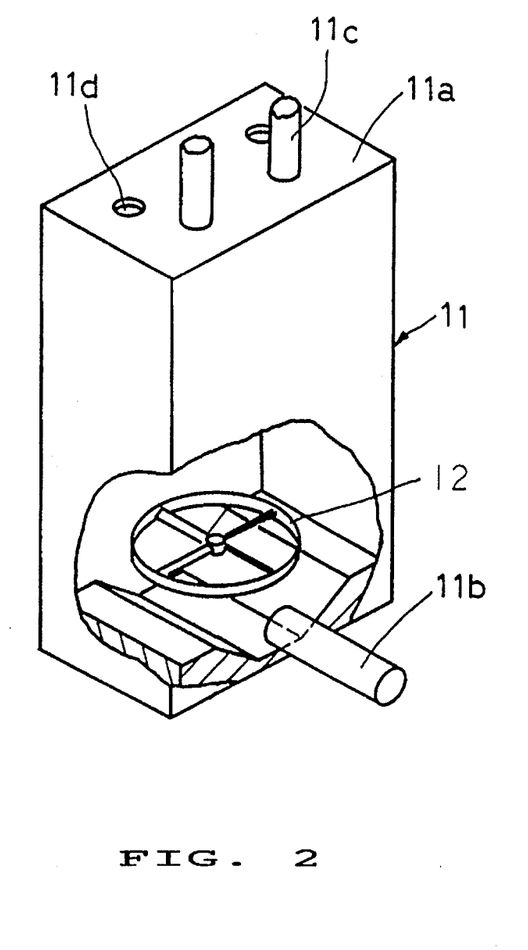
FIG. 2 is a perspective diagram of a reactor installed in the detector of one preferred embodiment.

As shown in FIG. 2, reactor 11 is a so-called rectangular cell having a rectangular section. Drain pipe 11b is associated with discharge tank 16 through valve 24 and pump 15. Pipes 11c connect to valve 5 and switching valve 10. Hole 11d for air-conditioning are provided on upper face 11a of the cell. The reactor can have a circular section other than a rectangular section. The hole 11d is helpful to prevent the inside of the reactor 11 from be applied with a back pressure in controlling the amount of fluid. Inside of reactor 11, magnetic stirrer bar 12 is placed.

Figure 3A:
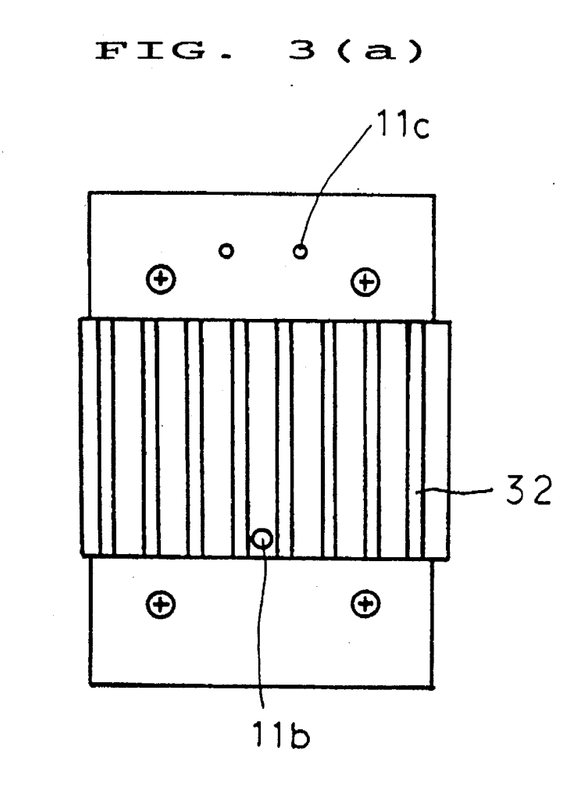
FIG. 3(a) is a front view of the reactor provided with a Peltier device in the detector of one preferred embodiment.
Figure 3B:
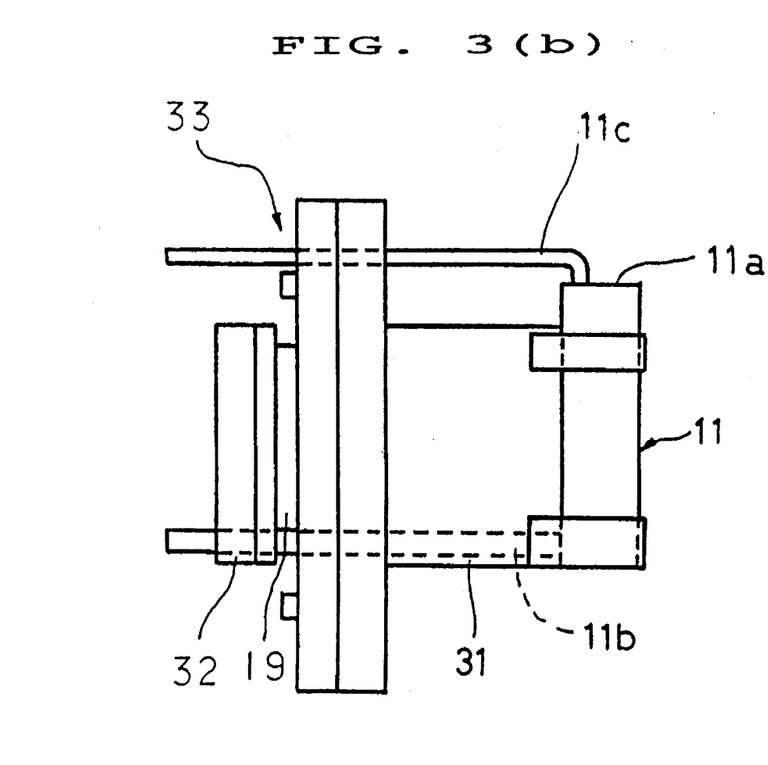
FIG. 3(b) is a side view of FIG. 3(a).

Referring to FIG. 3(a), reference numerals 11c, 11b and 32 denote inlets, an outlet and aluminum fins, respectively. Referring to FIG. 3(b), reactor 11 is fixed on one face of aluminum block 31, and thermostat 33 attached with Peltier device 19 is placed near reactor 11. Peltier device 19 is fixed on the other face of aluminum block 31. Aluminum fins 32 are attached on the opposite side of Peltier device 19. Peltier device 19 is attached to reactor 11 through block 31 having a large thermal capacity so that a rapid change-in temperature is controlled when solutions are introduced to reactor 11 or Peltier device 19 is heated. The whole detector is in air-conditioned room 17 of FIG. 1 so that steady examination is performed independently of temperature conditions.

Figure 4:
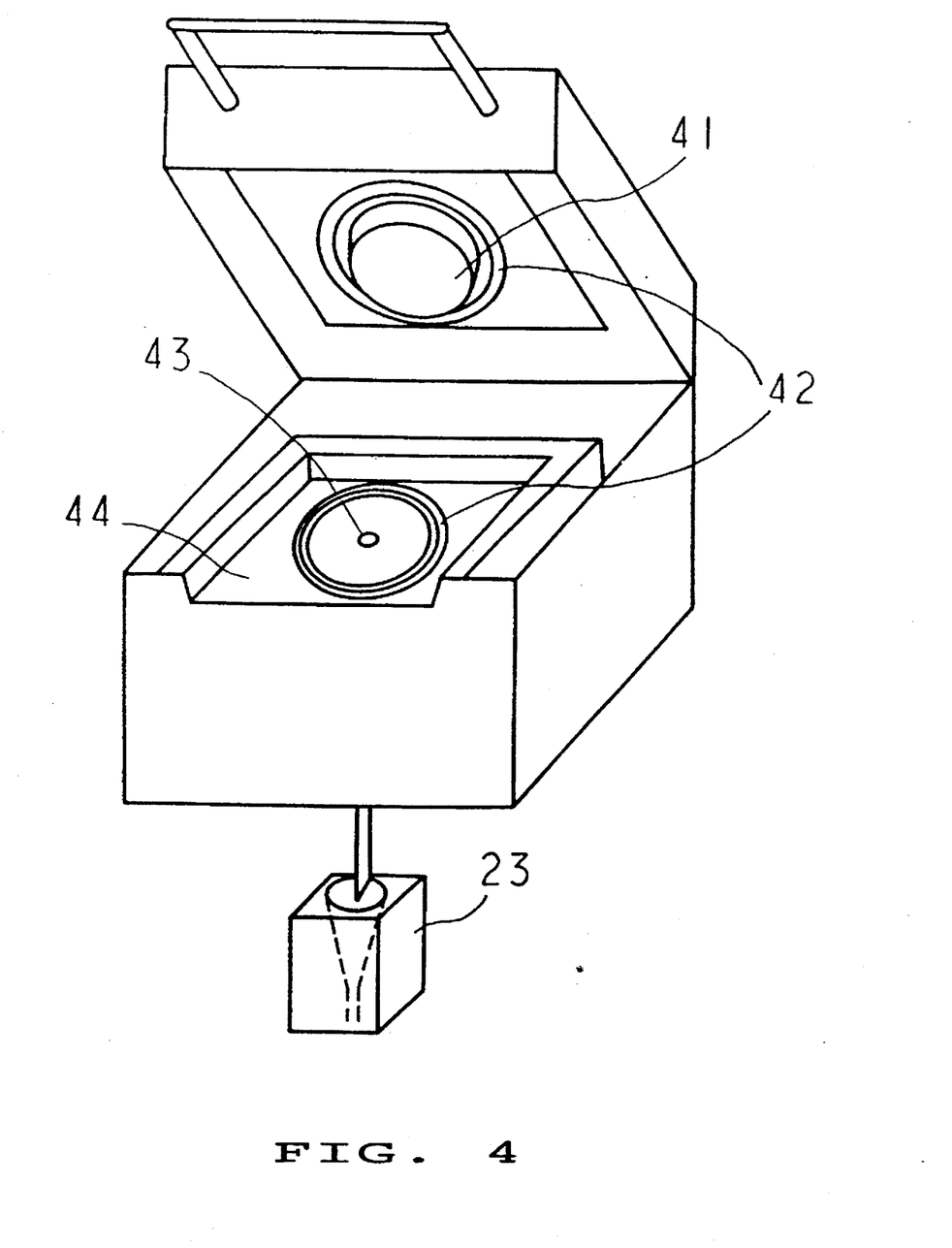
FIG. 4 is a perspective diagram of the elution device of the detector of one preferred embodiment.

Referring to FIG. 4, elution device 21 has piston 41, O-ring 41, inlet/outlet 43 and filter-installing part 44.

Further, computer 20 shown in FIG. 1 controls pumps 7, 8 and 9, valves 4, 5, 6, 10, 22 and 24, and magnetic stirrer 13. Computer 20 receives data from fluorescent detector 14 and processes the data to facilitate detection.

A preferred fluorescent intensity for cocaine or MA detection is 550 to 640 nm, particularly 590 nm at which cocaine or MA emits the strongest fluorescence. The 550 nm excitation light is most suitable for a high fluorescence intensity. However, taking stray light into consideration, excitation around 530 nm is favorable.

The preferred embodiments will be explained in detail.

High performance liquid chromatography (HPLC) was conducted under the following condition:

System: WATERS, 600 system, produced by Millipore Corporation

Detector: MCPD3600 produced by OHTSUKA DENSHI, Japan

Column: WATERS (15 μ, 100 nm, 7.9 mm×30 cm) produced by Millipore Corporation

Solvent: methanol/hydrochloric acid (0.01N)=3/2

Rate: 2.0 ml/min

Determination: made with an area of absorbance peak at 550 nm

EXAMPLE 1

(Preparation of Trimethyl Indolenium Salt)

2,3,3-Trimethylindolenine (10 g, MW=159.2, 0.063 mol) was mixed with chloroiodopropane (50 g, MW=204.4, 0.24 mol) in benzene (30 ml), and the mixture was heated in a nitrogen atmosphere at 80° C. for 6 h. Benzene evaporated during the reaction. The resulting product was cooled down and repeatedly washed with diethyl ether to form a pale red powder. The powdery product was identified as 1-(3-iodopropyl)-2,3,3-trimethyl indolenium chloride (MW=363.5) by NMR. The yield was 20 g (87%).

Table 1 shows the structure of trimethylindolenium salt and the chemical shifts of $^1$H-NMR in deuterated chloroform and the assignment of each peak.

TABLE 1

| Chemical Shift (δ, ppm) | Number of Hydrogen | Number of Peak | Assigned Carbon No. |
| --- | --- | --- | --- |
| 1.56 | 6 | 1 | 13 |
| 2.42 | 2 | 5 | 11 |
| 2.87 | 3 | 1 | 9 |
| 3.44 | 2 | 3 | 12 |
| 4.5 | 2 | 3 | 10 |
| 7.64 | 2 | m | 3, 4 |
| 7.85 | 1 | m | 5 |
| 7.99 | 1 | m | 6 | m: many

EXAMPLE 2

(Preparation of Iodopropyl Derivative)

The trimethyl indolenium salt obtained in Example 1 (4.4 g, 12.10 mmol) was dissolved in ethanol (200 ml). Dimethylaminobenzaldehyde of Formula IX having a molecular weight of 149.19 (1.81 g, 12.10 mmol) was added to this mixture, which was refluxed for 2 h. The reaction mixture was cooled to room temperature. The resulting precipitate was collected by filtration, and washed with ether. The product was subjected to recrystallization from ethanol to form an iodopropyl derivative (6.3 g, MW=494.7). The yield was 100%.

Table 2 shows the structure of the iodopropyl derivative and the chemical shifts of $^1$H-NMR in deuterated chloroform and the assignment of each peak.

TABLE 2

| Chemical Shift (δ, ppm) | Number of Hydrogen | Number of Peak | Assigned Carbon No. |
| --- | --- | --- | --- |
| 1.77 | 6 | 1 | 19 |
| 2.35 | 2 | 5 | 17 |
| 3.19 | 6 | 1 | 15 |
| 3.43 | 2 | 3 | 18 |
| 4.52 | 2 | 3 | 16 |
| 6.91 | 2 | 2 | 13 |
| 7.23 | 1 | 2 | 9 |
| 7.48, 7.46 | 2 | m | 4, 5 |
| 7.73, 7.79 | 2 | m | 3, 6 |
| 8.11 | 2 | 2 | 12 |
| 8.37 | 1 | 2 | 10 | m: many

EXAMPLE 3

(Preparation of Norcocaine)

Cocaine (1.0 g, 3.29 mmol) was dissolve in a mixed solvent of acetonitrile (55 ml) and water (110 ml). Acetic acid (1 ml) was added to the mixture to form a weak acidic solution. To this solution was added an aqueous solution (42 ml) of potassium permanganate (1.06 g, 7.55 mmol) dropwise over 8 h. After the addition, the mixture was stirred overnight at room temperature. The resulting precipitate was removed by filtration, and potassium carbonate was added to the filtrate to form a basic solution. The solution was extracted with diethyl ether three times, and anhydrous potassium sulfate was added to the organic layer for dryness. The ether was distilled off under reduced pressure. The product was purified by silica gel thin-layer chromatography (eluent: ammonia-saturated chloroform) to form norcocaine (536 mg, MW=289.4, Yield: 56%).

Table 3 shows the structure of norcocaine and the chemical shifts of $^1$H-NMR in deuterated chloroform and the assignment of each peak.

TABLE 3

| Chemical Shift (δ, ppm) | Number of Hydrogen | Number of Peak | Assigned Carbon No. |
| --- | --- | --- | --- |
| 1.70–2.10 | 6 | m | 4, 6, 7 |
| 2.40 | 1 | 1 | 8 |
| 3.07 | 1 | 4 | 2 |
| 3.64 | 3 | 1 | 10 |

TABLE 3-continued

| Chemical Shift (δ, ppm) | Number of Hydrogen | Number of Peak | Assigned Carbon No. |
| --- | --- | --- | --- |
| 3.70–3.74 | 2 | m | 1, 5 |
| 5.55 | 1 | 5 | 3 |
| 7.43 | 2 | m | 13 |
| 7.54 | 1 | 3 | 14 |
| 7.96 | 2 | m | 12 | m: many

EXAMPLE 4

(Preparation of CCIMC)

Iodopropyl derivative prepared in Example 2 (100 mg, 0.20 mmol) and norcocaine prepared in Example 3 (292 mg, 1.01 mmol) were dissolved in chloroform (30 ml). This mixture was refluxed in nitrogen atmosphere for 8 h. The reaction mixture was cooled to room temperature, and added to an about 1000 ml of ether while stirring. The resulting precipitate was collected by filtration and washed with ether to form CCIMC (125 mg, MW=655.5). The yield was 94%.

Table 4 shows the structure of CCIMC and the chemical shifts of $^1$H-NMR in deuterated chloroform and the assignment of each peak.

TABLE 4

| Chemical Shift (δ, ppm) | Number of Hydrogen | Number of Peak | Assigned Carbon No. |
| --- | --- | --- | --- |
| 1.79 | 6 | 1 | 16 |
| 1.92 | 4 | 3 | 21, 22 |
| 2.12 | 2 | 4 | 24 |
| 2.30 | 1 | m | 20 |
| 2.45 | 2 | m | 18 |
| 3.13 | 6 | 1 | 15 |
| 3.28 | 3 | m | 23, 26 |
| 3.70 | 3 | 1 | 33 |
| 4.17 | 2 | 3 | 17 |
| 4.79 | 2 | 3 | 19 |
| 5.46 | 1 | m | 25 |

TABLE 4-continued

[Chemical structure diagram with numbered atoms: aromatic ring system (positions 1-10) connected via vinyl group to dimethylamino-phenyl (11-15), with N-ethyl chain (17-19) and COOCH₃ ester group (20-33) attached through bicyclic structure to benzoate ring]

| Chemical Shift (δ, ppm) | Number of Hydrogen | Number of Peak | Assigned Carbon No. |
|---|---|---|---|
| 6.79 | 2 | 2 | 13 |
| 7.40–7.50 | 4 | m | 4, 5, 30 |
| 7.55–7.65 | 4 | m | 3, 6, 9, 31 |
| 7.94 | 2 | 2 | 29 |
| 8.01 | 2 | 2 | 12 |
| 8.07 | 1 | 2 | 10 | m: many

EXAMPLE 5

(Measurement of Change in Fluorescence Intensity of CCIMC)

A phosphate buffer solution (PBS) of CCIMC prepared in Example 4 (1487.5 μl, Final concentration: $7.09 \times 10^{-6}$ M) was stirred at 25° C. for 1 m. A fluorescence intensity of 590 nm using the solution was measured at 530 nm excitation wavelength. The intensity was 110.4. To this solution was added a solution of cocaine antibody having a final concentration of $1 \times 10^{-6}$ M (114.3 μl), and the mixture was stirred at 25° C. for 1 m. A fluorescence intensity was similarly measured so that the intensity was found to have increased to 165.5.

To this solution was added a solution of cocaine having a final concentration of $1.9 \times 10^{-4}$ M (150 μl). A fluorescence intensity of 590 nm was similarly measured at 530 nm excitation wavelength. The intensity was 113.9. The measurement confirmed that the bonding of CCIMC to the antibody was completely inhibited.

The measurement of fluorescence intensities was similarly performed using solutions of cocaine antibody having a final concentration of $7.71 \times 10^{-5}$ M, $1.94 \times 10^{-5}$ M, $7.84 \times 10^{-6}$ M, $1.97 \times 10^{-6}$ M, $7.96 \times 10^{-7}$ M, $1.99 \times 10^{-7}$ M, $7.93 \times 10^{-8}$ M, $1.84 \times 10^{-8}$ M and $6.21 \times 10^{-9}$ M. The intensities were 116.6, 125.1, 135.2, 149.8, 156.5, 161.1, 162.8, 163.7 and 165.1, respectively.

Figure 5:
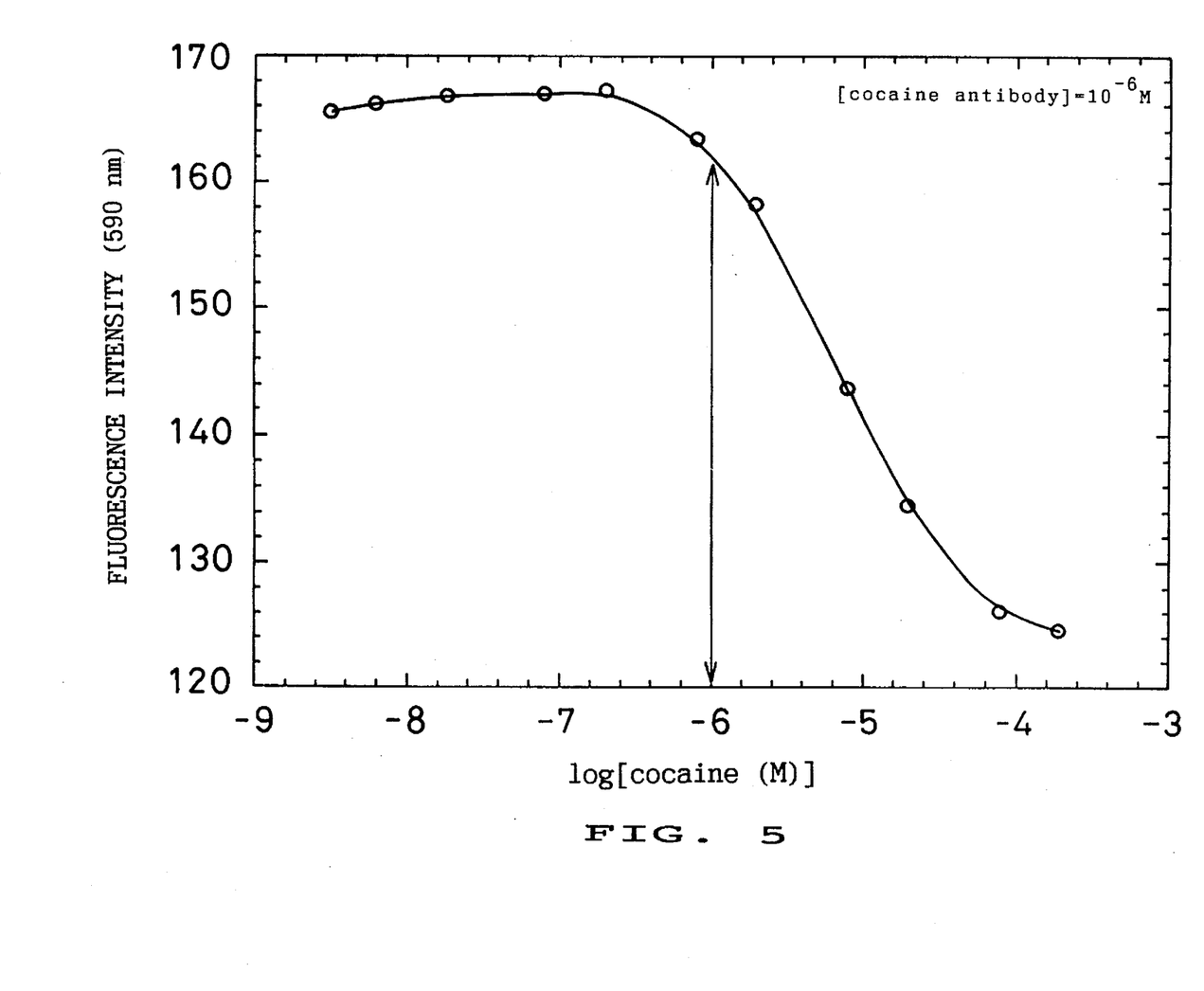
FIG. 5 shows a fluorescence characteristics of a solution containing the labelling compound of Formula I and cocaine antibody to which cocaine is added in one preferred embodiment.

FIG. 5 shows a fluorescence curve of a complex of CCIMC and $10^{-6}$ M cocaine antibody in one embodiment. The curve shows that CCIMC leaves cocaine antibody and bonds to a newly added cocaine, decreasing the fluorescence intensity.

EXAMPLE 6

(Preparation of Acetyl Derivative)
3-Bromopropylacetate (BPA) was prepared as follows.

Bromopropanol (102.520 g, MW=139.00, 0.7376 mol) in benzene (50 ml) was gradually added to acetic anhydride (91.364 g, MW=102.99, 0.8871 mol) in benzene (50 ml) so as to prevent generation of heat. The mixture was stirred overnight at room temperature. Gas-liquid chromatography confirmed that the whole amount of bromopropanol completely reacted. The reaction mixture was washed with pure water five times to hydrolyze unreacted acetic arthydride and remove acetic acid. The benzene layer was dried with magnesium sulfate for about 24 h, and benzene was evaporated. After distillation, a fraction of 66 mm Hg, 113–115° C. was extracted.

(Alkylation of 2,3,3-Trimethylindolenine)

2,3,3-Trimethylindolenine (TMI, 43.9 g, 0.2758 mol) and BPA having a molecular weight of 181.3 prepared above (50 g, 0.2758 mol) were mixed in benzene (30 ml), and the solution mixture was heated in a nitrogen atmosphere at 130° C. for 6 h. Benzene evaporated during the reaction. The reactant was cooled to be a tar-like substance. The product was washed repeatedly with diethyl ether to form a pale red powder. This powdery product was identified as 1-(3-acetylpropyl)-2,3,3-trimethylindolenium bromide (APTMI, MW=340.26). The yield was 81 g, 0.2380 mol, 86.3%. The tar-like product seemed to strongly bond to unreacted TMI, and it was difficult to purify the product. Therefore, to purify an amount of the tar-like product, small amounts of that were pulverized in ether in a mortar before purification. After preliminary purification, the resulting solid product was dispersed in ether in a flask. The product was subjected to ultrasonic wave irradiation for 0.5–2 h before secondary purification. The purity at that time was sufficient for synthesis. For analysis, a further purification was performed by dissolving the product in a small amount of acetone and diluting it with benzene.

(Preparation of Acetyl Derivative)

Solution No. 1 was formed by gradually heating and dissolving APTMI (9.9906 g, 0.0294 mol) in ethanol (75 ml). Solution No. 2 was formed by gradually heating and dissolving p-dimethylamino benzaldehyde (4.5994 g, 0.0308 mol) in ethanol (50 ml). Solution Nos. 1 and 2 were mixed to quickly turn reddish purple at room temperature. After 2-hour reflux, the mixture was cooled overnight at room temperature for about 24 h to form a purple precipitate. This precipitate was collected by filtration and washed with benzene to form a solid product of 9.7609 g. NMR analysis identified the product as a compound of Formula VI wherein the halogen atom was bromine (MW=471.44). After distilling off the solvent, the filtrate was formed to a brown glue-like product. Attention should be given to a sudden boiling. The glue-like product was dried over diphosphous pentaoxide in vacuum at 60° C. to form a solid. This solid was dissolved in heated ethanol (50 ml) and allowed to stand overnight at −20° C. to form a purple crystal. The crystal was collected by filtration and washed with benzene. The above procedure readily improved the purity of the product. The yield of the product was 13.92 g, 0.0295 mol, 100%.

Table 5 shows the structure of the acetyl derivative and the chemical shifts of $^1$H-MR in deuterated chloroform and the assignment of each peak.

TABLE 5

| Chemical Shift (δ, ppm) | Number of Hydrogen | Number of Peak | Assigned Carbon No. |
| --- | --- | --- | --- |
| 1.78 | 6 | 1 | 16 |
| 1.92 | 3 | 1 | 21 |
| 2.37 | 2 | 5 | 18 |
| 3.2 | 6 | 1 | 15 |
| 4.32 | 2 | 3 | 19 |
| 5.07 | 2 | 3 | 17 |
| 6.84 | 2 | 2 | 13 |
| 7.51 ~ 7.39 | 4 | m | 3 ~ 6 |
| 7.82 | 1 | 2 | 9 |
| 8.06 | 1 | 2 | 10 |
| 8.29 | 2 | b | 12 | m: many, b: distiguishable

EXAMPLE 7

(Preparation of Hydroxy Derivative)

The acetyl derivative prepared in Example 6 (7.6582 g, 16.24 mmol) was dissolved in methanol (500 ml). To the solution was added 10-N sodium hydroxide (3 ml, 30 mmol) while stirring. The reaction mixture was allowed to stand at room temperature. In some minutes, the solution, which was first dark purple, was colorless. Liquid chromatography confirmed that the whole amount of the acetyl derivative completely reacted in one hour, though about 25% of the compound remained unreacted in half an hour. After 2-h stirring, acetic acid (5.1019 g, 84.96 mmol) was added so that the color of the solution quickly returned to the initial color. Then, methanol and acetic acid were removed by evaporation. Chloroform was added to the almost dried product, followed by filtration of undissolved sodium acetate. The filtrate was again evaporated, and the resulting paste-like product of dark purple was ultrasonically washed with diethyl ether to form a purple solid. This product was dried under vacuum at 60° C. together with diphosphous pentaoxide. The yield of the product having a molecular weight of 429.5 was 5.7413 g, 13.37 mmol, 82.3%. IR spectrum according to KBr tablet method of the starting compound, that is, acetyl derivative was compared with the spectrum of the above prepared acetyl derivative. Consequently, peaks at 1700 and 1240 cm$^1$ due to an acetyl group of the acetyl derivative completely disappeared. Therefore, it was concluded that the product of this example was the intended hydroxy derivative, the compound of Formula V wherein X is a bromine atom.

EXAMPLE 8

(Preparation of Methanesulfonate Derivative)

The hydroxy derivative prepared in Example 7 (1.00 g, 2.33 mmol) and methanesulfonic anhydride (2.5377 g, MW=174.2, 14.57 mmol) were dissolved in chloroform (15 ml). This mixture was stirred at room temperature for 13 days, and washed with 3% solution of salt three times. The chloroform layer was dried over magnesium sulfate. After 20 days, magnesium sulfate was filtrated, and the solvent was distilled off, followed by washing the resulting product with diethyl ether. The yield of the product having a molecular weight of 507.49 was 0.6853 g, 1.35 mmol, 58.0%.

The retention time of the hydroxy derivative in HPLC was about 11 min while that of the product of this example was about 17 min. Further, it became clear that the final product contained no starting compound.

EXAMPLE 9

The methanesulfonate derivative prepared in Example 8 (55.1 mg, 0.109 mmol) and MA (133.8 mg, MW=149.24, 0.897 mmol) were dissolved in acetic acid (235.7 mg), and the mixture was stirred at 80° C. for 2 h. The reaction was observed by HPLC. After that reaction, a product of 10 wt % was found at the position of 11-min in an HPLC chart. After 17 h, the whole methanesulfonate derivative was converted to the compound having a peak at the position of 11-min. The inventors concluded that the product was the intended labelling compound of Formula N (MAIMC), judging from the chemical structure of the compounds prepared in Examples 6, 7 and 8, the fact that the reaction of this example was free from any side reaction, and the general reaction path between methanesulfonates and amines.

The product was ultrasonically washed with diethyl ether three times. HPLC proved that the product was pure. The yield was almost 100%.

EXAMPLE 10

(Measurement of Change in Fluorescence Intensity of MAIMC)

A PBS of MAIMC prepared in Example 9 (1600 μm, Final concentration: $8.6 \times 10^{-6}$ M) was stirred at 25° C. for 1 m. A fluorescence intensity of 590 nm using the solution was measured at 530 nm excitation wavelength. The intensity was 32.0. To this solution was added 100 μl of MA antibody having a final concentration of $6.1 \times 10^{-6}$ M, and the mixture was stirred at 25° C. for 1 m. The fluorescence intensity was similarly measured, and the intensity was found to have increased to 54.8.

To this solution was added a PBS (100 μl) of MA having a final concentration of $2.3 \times 10^{-5}$ M. A fluorescence intensity of 660 nm was similarly measured at 600 nm excitation wavelength. The intensity was 31.0. The measurement confirmed that the fluorescence intensity increased due to the fact that bonding of MAIMC to the antibody was completely inhibited by the addition of MA.

The measurement of fluorescence intensity was similarly performed using a PBS instead of a solution of MA in PBS. The fluorescence intensity was found to be 53.0. Therefore, it is concluded that MA was detected by the labelling compound of this example in the immunological methodology.

EXAMPLE 11

The change in fluorescence intensities due to the bonding of cocaine antibody and MA antibody to a mixed solution of the labelling compounds of Formulas I and II was examined by the detector shown in FIG. 1.

The mixed color solution (1.25 ml) for elution in container 1 was injected to pump 7 through valve 4. This solution was prepared by mixing equal amounts of aqueous solutions of the compounds prepared in Examples 4 and 9 each having a concentration of $6 \times 10^{-7}$M.

The solution in pump 7 was once conveyed to reservoir 23 through valves 4 and 22 so that air bubbles were removed.

The solution of 1.25 ml in reservoir 23 was sucked in pump 9 through valves 10 and 6. The solution of 1.10 ml was injected to rectangular cell 11 in fluorescence detector 14 (produced by NIHON BUNKO, FP-821) by switching valve 10. Rectangular cell 11 having an outlet in the upper face enabled injection of solutions quantitatively because the cell was free from back pressure. The fluorescence intensity of 660 nm of the solution was measured at 600 nm excitation wavelength while stirring the solution with magnetic stirrer bar 12, and the intensity was 6.44.

Then, the MA antibody solution of 0.08 ml having a concentration of $1 \times 10^{-5}$M in container 2 was sucked in pump 8 through valve 5. The whole amount of the antibody solution was injected from pump 8 to cell 11 by switching valve 5. The fluorescence intensity of 660 nm of the solution was measured at 600 nm excitation wavelength while stirring the solution with magnetic stirrer bar 12, and the intensity was found to have increased to 6.55. This measuring process was carried out using various solutions each having a different antibody concentration. The inside of the cell 11 and all tubes were repeatedly washed with the color solution before a next measurement. Such washing step was performed before every measurement.

The steps of measuring intensities of 590 nm at 530 nm excitation wavelength were similarly carried out using a $1 \times 10^{-5}$M cocaine antibody instead of the above MA antibody.

A fluorescence intensity of 660 nm was similarly measured at 600 nm excitation wavelength by adding a predetermined concentration of MA to the mixed color solution containing MA antibody and cocaine antibody so that a fluorescence characteristic curve of the solution was obtained.

A fluorescence intensity of 590 nm was similarly measured at 530 nm excitation wavelength by adding a predetermined concentration of cocaine to the mixed color solution so that a fluorescence characteristic curve of the solution, like FIG. 5, was obtained.

To actually detect cocaine or MA out of an air sample, a filter having been exposed to the air sample is attached in filter-install part 44 in elution device 21. Cocaine or MA is eluted from the filter to the elution color solution. The existence and concentration of cocaine or MA are determined by the fluorescence intensity of the eluate with reference to the above characteristic curves.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A labelling color for detecting cocaine of Formula I

Formula I wherein X represents a halogen atom.

2. A labelling color for detecting methamphetamine of Formula II

Formula II wherein X represents an anion.

3. A method of detecting cocaine, comprising the steps of adding a labelling color of Formula I Formula I wherein X represents a halogen atom to a first solution of cocaine antibody to form a labelling color-cocaine antibody complex, measuring the fluorescence of the first solution, adding a sample containing an unknown amount of cocaine to the first solution to form a second solution, measuring the fluorescence of the second solution, and correlating any change in the fluorescence between the first and second solutions to the concentration of cocaine in the sample.

4. A method of detecting methamphetamine, comprising the steps of adding a labelling color of Formula II wherein X represents an anion to a first solution of methamphetamine antibody to form a labeling color-methamphetamine antibody complex, measuring the fluorescence of the first solution, adding a sample containing an unknown amount of methamphetamine to the first solution to form a second solution, measuring the fluorescence of the second solution, and correlating any change in the fluorescence between the first and second solutions to the concentration of methamphetamine in the sample.

5. A detector for cocaine comprising containers for storing each of a first solution containing a labelling color of Formula I wherein X represents a halogen atom and a second solution containing cocaine antibody, an eluting means for eluting a sample with a buffer to form a sample solution, a reactor for reacting said sample solution with said first solution containing said labelling color and said solution containing cocaine antibody, a supplying means for supplying each of the sample solution and said solution containing cocaine antibody to said reactor, and a fluorescent detector for measuring fluorescences of the first and second solutions, and a mixture of the sample solution and the first and second solutions.

6. A detector for methamphetamine comprising containers for storing each of a first solution containing a labelling color of Formula II wherein X represents an anion and a second solution containing methamphetamine antibody, an eluting means for eluting a sample with a buffer to form a sample solution, a reactor for reacting said sample solution with said first solution containing said labelling color and said solution containing methamphetamine antibody, a supplying means for supplying each of the sample solution and said solution containing methamphetamine antibody to said reactor, and a fluorescent detector for measuring fluorescences of the first and second solutions, and a mixture of the sample solution and the first and second solutions.

7. The detector according to claim 5 or 6, wherein said supplying means is a syringe pump and a valve.

8. The detector according to claim 5 or 6, wherein said reactor is a rectangular cell having an outlet and a hole in an upper face and a nozzle for exhaustion at the bottom.

9. The detector according to claim 5 or 6, wherein a stirring means for stirring solutions is provided in the reactor, and said stirring means is driven by magnetic force.

10. The detector according to claim 5 or 6, wherein a thermostat using a Peltier device is provided in the reactor.

11. The detector according to claim 5 or 6, wherein the containers and supplying means are provided within an air-conditioning thermostat.

12. A methanesulfonate derivative of Formula IV wherein X is an anion.

13. An acetyl derivative of Formula VI wherein X represents an anion.

14. A method of preparing a labelling color of Formula I wherein X represents a halogen atom, comprising the steps of dissolving a propyl halide derivative of Formula III wherein $X_1$ and $X_2$ represents the same or different halogen atom in an organic solvent, adding norcocaine of Formula VII to the solution, and heating the solution.

15. A method of preparing a propyl halide derivative of Formula III wherein $X_1$ and $X_2$ represents the same or different halogen atom, comprising the steps of dissolving a trimethyl indolenium salt of Formula VIII wherein $X_1$ and $X_2$ is the same or different halogen atom, and dimethylamino benzaldehyde of Formula IX in an organic solvent, and heating the solution.

16. A method of preparing a labelling color of Formula II

Formula II wherein X represents an anion, comprising the steps of providing a methanefulfonate derivative of Formula IV Formula IV wherein X is an anion and substituting methamphetamine for a methanesulfonate group of the methanesulfonate derivative of Formula IV in an acidic solvent.

* * * * *